(12) United States Patent
Patterson et al.

(10) Patent No.: US 8,332,053 B1
(45) Date of Patent: Dec. 11, 2012

(54) METHOD FOR FABRICATION OF A STRETCHABLE ELECTRONIC SKIN

(75) Inventors: Pamela R. Patterson, Los Angeles, CA (US); Kevin S. Holabird, Los Angeles, CA (US); Christopher P. Henry, Thousand Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 534 days.

(21) Appl. No.: 12/431,042

(22) Filed: Apr. 28, 2009

(51) Int. Cl.
*A61N 1/00* (2006.01)

(52) U.S. Cl. ........................................ 607/152; 600/393

(58) Field of Classification Search .................. None
See application file for complete search history.

(56) References Cited

U.S. PATENT DOCUMENTS

| | | | |
|---|---|---|---|
| 4,634,623 A | | 1/1987 | Watkins |
| 6,743,982 B2 | | 6/2004 | Biegelsen et al. |
| 6,825,539 B2 | | 11/2004 | Tai et al. |
| 2004/0243204 A1* | | 12/2004 | Maghribi et al. ............ 607/115 |
| 2010/0053907 A1* | | 3/2010 | Soares et al. ................. 361/728 |
| 2011/0245645 A1* | | 10/2011 | Kenngott et al. ............ 600/373 |

OTHER PUBLICATIONS

LaCour, Stephanie P. et al., Stretchable gold conductors on elastomeric substrates, Applied Physics Letters, Apr. 14, 2003, p. 2404-2406, vol. 82, No. 15.

Someya, Takao et al., A large-area, flexible pressure sensor matrix with organic field-effect transistors for artificial skin applications, PNAS, Jul. 6, 2004, p. 9966-9970, vol. 101, No. 27 (www.pnas.org/cgi/doi/10.1073/pnas.0401918101).

Wagner, Sigurd et al., Electronic skin; architecture and components, Physica E 25 2004, p. 326-334 (doi:10.1016/j.physe.2004.06.032).

Gray, Darren S. et al., High-Conductivity Elastomeric Electronics, Advanced Materials, Mar. 5, 2004, vol. 16, No. 5 (doi:10.1002/adma.200306107).

Kim, Dae-Hyeong, et al., Materials and noncoplanar mesh designs for integrated circuits with linear elastic responses to extreme mechanical deformations, PNAS, Dec. 2, 2008, p. 18675-18680, vol. 105, No. 48 (www.pnas.org/cgi/doi/10.1073/pnas.0807476105).

Someya, Takao et al., Conformable, flexible, large-area networks of pressure and thermal sensors with organic transistor active matrixes, PNAS, Aug. 30, 2005, p. 12321-12325, vol. 102, No. 35 (www.pnas.org/cgi/doi/10-1073/pnas.0502392102).

\* cited by examiner

*Primary Examiner* — Duy Deo
(74) *Attorney, Agent, or Firm* — Christopher R. Balzan

(57) ABSTRACT

In one implementation, a method of fabrication of stretchable electronic skin is provided. The method may include receiving an elastic material net. An elastic conductor mesh is formed on the elastic material net. A device is electrically bonded to the elastic conductor mesh. The implementation may further include forming a mold comprising a net pattern on a substrate and creating the elastic material net by coating the mold with an elastic material precursor, and then removing the elastic net from the substrate with the elastic conductor thereon. In one embodiment, a stretchable electronic skin including a net structure having a non-conducting elastic material with an elastic conductor mesh formed on the non-conducting elastic material, and a device electrically connected to the elastic conductor mesh.

15 Claims, 6 Drawing Sheets

METHOD FOR FABRICATION OF A STRETCHABLE ELECTRONIC SKIN

BACKGROUND

Stretchable circuits enable electronics onto non-planar 3D surfaces. Distinguished from flexible circuits, which can simply be place on a 2D non-planar surface, stretchable circuits can support biaxial strain rather than simply uniaxial strain. A stretchable circuit can be wrapped around 3D objects. Microscale devices such as a mini UAV, need to not only put electronics on non-planar surfaces, but also embed sensors all over a mini-structure to detect temperature, pressure, force, or other input that a mini system may want to detect, i.e. aeronautical, biological, or other related sensors.

Systems with coiled interconnects, which are 3D in nature, are not readily created with standard micro-fabrication planar processing techniques and hence are not easily integrated. On the other hand, standard metal thin films of aluminum, wire bonding, and soldering for the electrical connections offer very limited stretchability. Conventional metal wires patterned on continuous sheets of an elastomer offer only uniaxial strain for micro-scale.

What is needed is a low cost stretchable electronic skin design and fabrication technique that provides a stretchable electronic circuit skin for integrating electronics over the structure of a microscale system. Moreover, what is needed is an easily manufactured stretchable electronic skin capable of a large amount of stretch.

SUMMARY

In one implementation, a method of fabrication of stretchable electronic skin is provided. The method may include receiving an elastic material net. An elastic conductor mesh is formed on the elastic material net. A device is electrically bonded to the elastic conductor mesh. The implementation may further include forming a mold comprising a net pattern on a substrate and creating the elastic material net by coating the mold with an elastic material precursor, and then removing the elastic net from the substrate with the elastic conductor thereon.

In one embodiment, a stretchable electronic skin including a net structure having a non-conducting elastic material with an elastic conductor mesh formed on the non-conducting elastic material, and a device electrically connected to the elastic conductor mesh.

BRIEF DESCRIPTION OF THE DRAWINGS

The features and advantages of the present invention will be better understood with regard to the following description, appended claims, and accompanying drawings where:

DESCRIPTION

Figure 1:
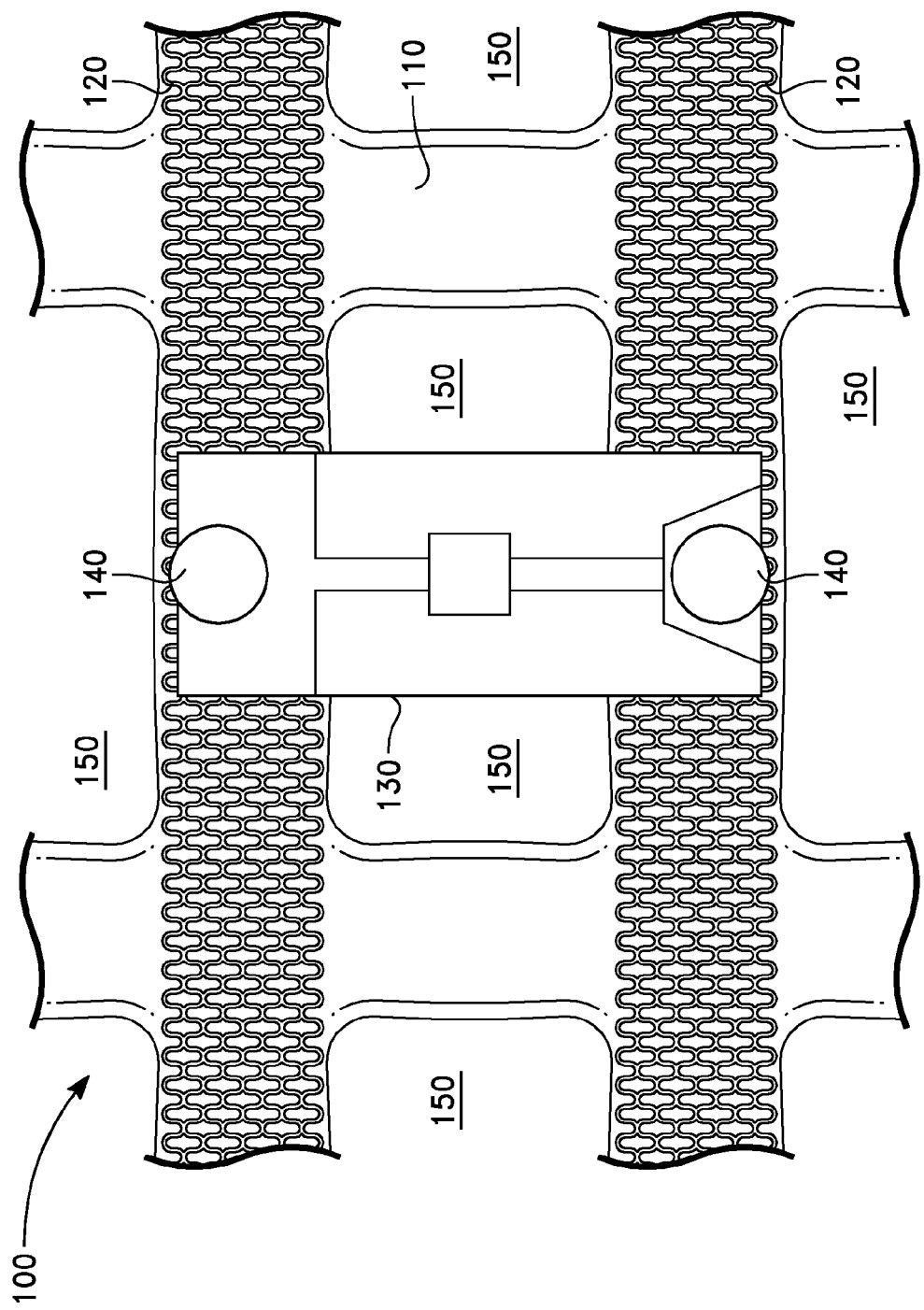
FIG. 1 shows an enlarged cut away top view of a stretchable electronic skin in accordance with one embodiment of the present invention.

FIG. 1 shows an enlarged cut away top view of a stretchable electronic skin 100 in accordance with one embodiment of the present invention. An elastomer net 110 has a stretchable conductor mesh 120 of metal or other elastic conductor thereon. The stretchable conductor mesh 120 may be a two dimensional conductor, deposited/etched on the elastomer net 110 using lithographic techniques. One or more devices 130 may be bonded to the conductor mesh 120 such as by solder 140 or other conductive bond. The elastomer net 110 with the device(s) 130 thereon may be stretched around an object or a complex topographical surface (not shown) to be conformal with it. The spaces 150 within the net 110 facilitate increased reversible stretch. The mesh 120 on net 110 allows greater reversible stretch and may be fabricated using planar processing techniques as discussed further below.

Figure 2:
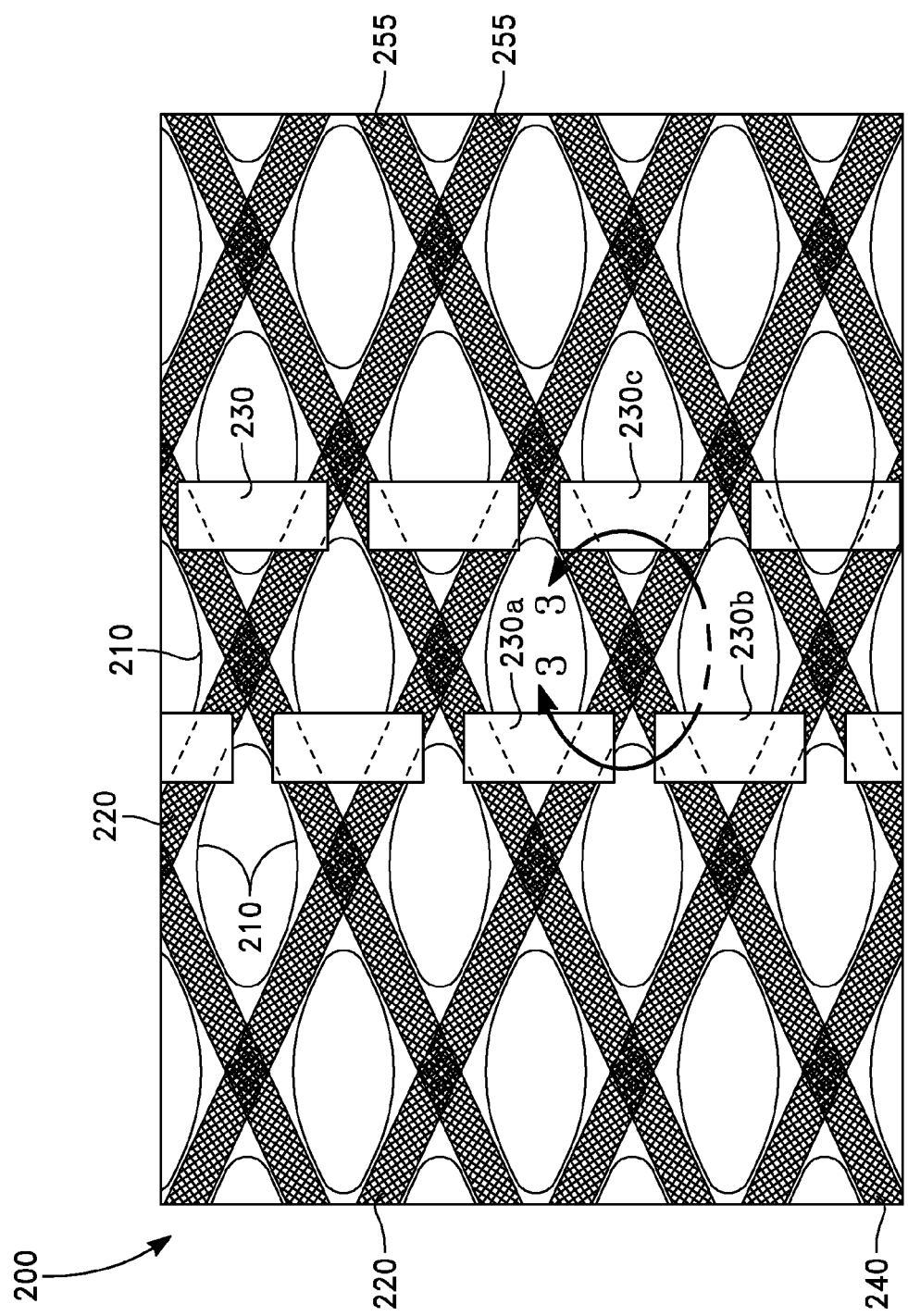
FIG. 2 is a top view of a stretchable electronic skin 200 in accordance with another embodiment.

FIG. 2 is a top view of a stretchable electronic skin 200 in accordance with another embodiment. In this embodiment, stretchable mesh conductors 220 and 240 on an elastomer net 210 form a row-column addressable circuit 255 to connect to two-terminal devices 230.

Figure 3:
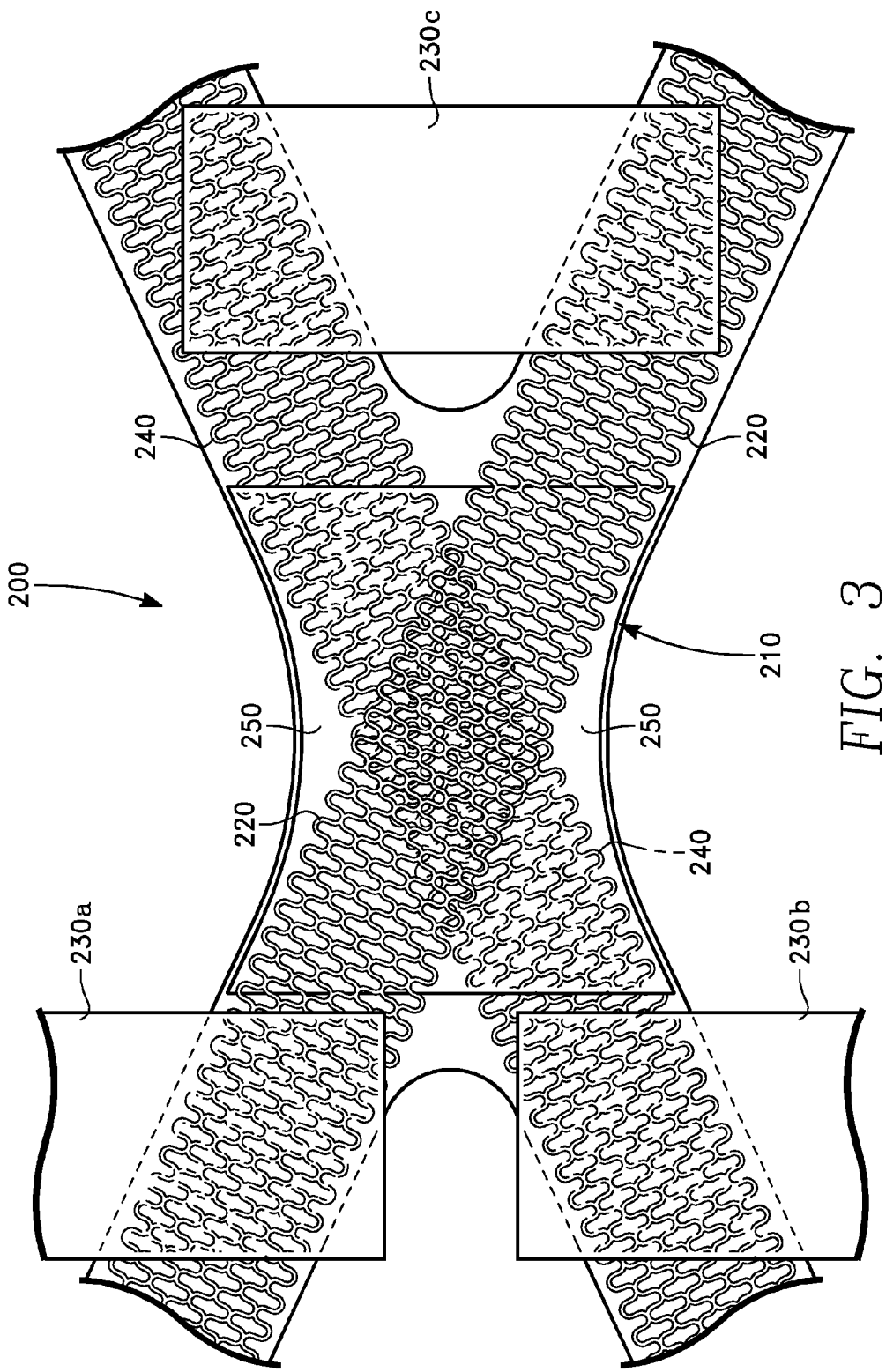
FIG. 3 is an enlarged exploded top view of the stretchable electronic skin along the 3-3 line of FIG. 2.

FIG. 3 is an enlarged exploded top view of the stretchable electronic skin 200 along the 3-3 line of FIG. 2. As illustrated in FIG. 3, an intermetal dielectric 250 may be interposed between the stretchable mesh conductors 220 and 240 within the elastomer net 210. Devices 230a, 230b, and 230c are secured to, and contact (not shown in FIG. 2 or 3), the stretchable mesh conductors 220 and 240.

Figure 4:
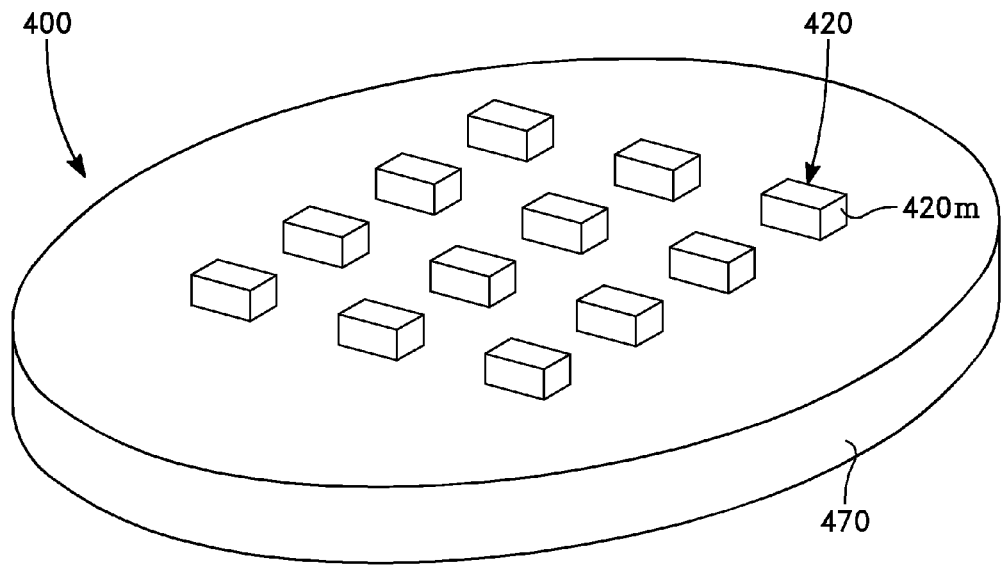
FIGS. 4 through 8 show an isometric view of a possible implementation for fabricating the stretchable electronic skin of FIG. 1.

FIGS. 4 through 8 show an isometric view of a possible implementation for fabricating the stretchable electronic skin 100 of FIG. 1. Referring to FIG. 4, in this implementation, silicon wafer is lithographically patterned to form a mold 400 of the reverse of the elastomer net (not shown).

The mold may be 160 micron thick on formed on a 4 inch diameter wafer 470 with SU-8, a photoactive epoxy 420, available from MICROCHEM, located in Newton, Mass. The photoactive epoxy 420 is capable of forming thick films in one application. The mold 400 could also be made from a pattern etched in a suitable substrate material e.g., silicon, or cut, formed, etc. in/of another known mold material.

Figure 5:
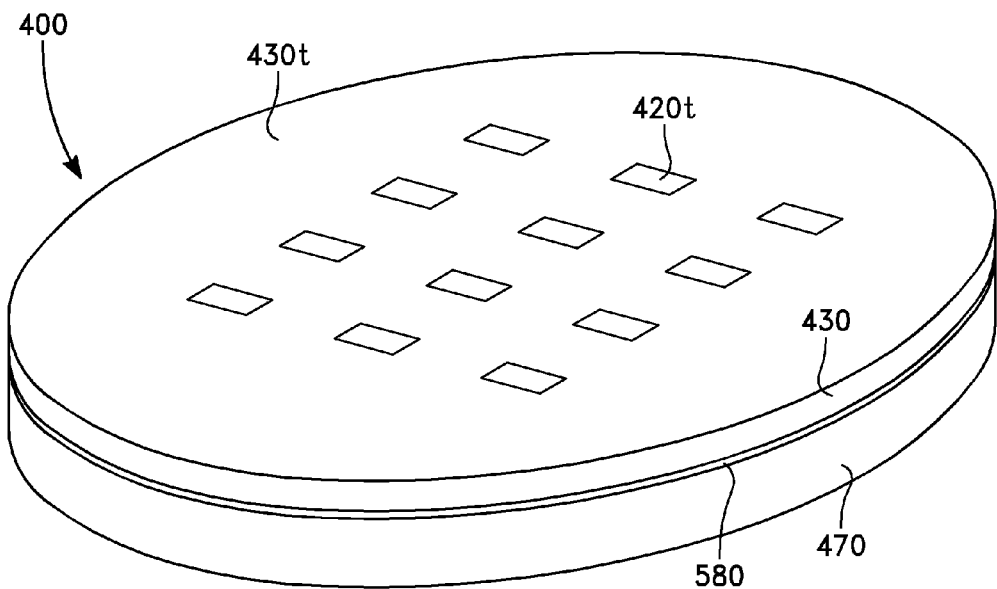

Shown in FIG. 5, a suitable elastomer material 430 is applied, such as silicone, for example SYLGARD 184, available from Dow Corning Corp., Midland, Mich. The silicone material 430 may be applied with a pour and spin on technique, to the mold 400, and the excess removed with a squeegee to remove the elastomer material 430 from the tops 420$t$ of the mesas 420$m$ (shown in FIG. 4) of the mold 400. The excess may be removed prior to solidifying the silicone material 430. This patterns spaces 150 in the elastomer net 110 referred to with reference to FIG. 1, and creates a flat surface 430$t$ for subsequent lithography. An optional mold coat layer 580 may be applied prior to applying the elastomer material 430, such as OMNICOAT available from Microchem Corp., located in Newton, Mass., to facilitate later release of the elastomer material 430 from the mold 400, as discussed below with reference to FIG. 8.

Figure 6:
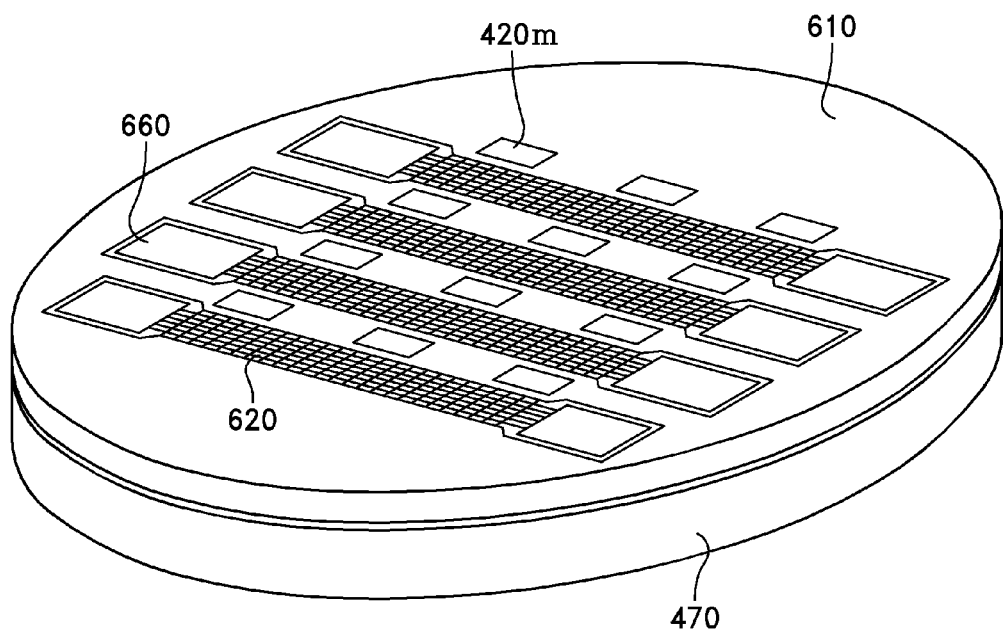

Turning to FIG. 6, a fine conductor mesh 620 is selectively deposited between the mesas 420$m$ in rows on the silicone material net 610 (FIG. 5) using a photo-resist lift-off technique. The conductive material of the conductor mesh 620 could be copper, gold, other high conductivity metal or alloy, or other flexible conductive material. Contacts 660 may also be patterned and deposited on the elastomer net 610 when forming the conductor mesh 620. The dimensions of the conductor mesh are only limited by the photolithographic technique used. Conductor widths on the order of 25 microns are typical.

Figure 7:
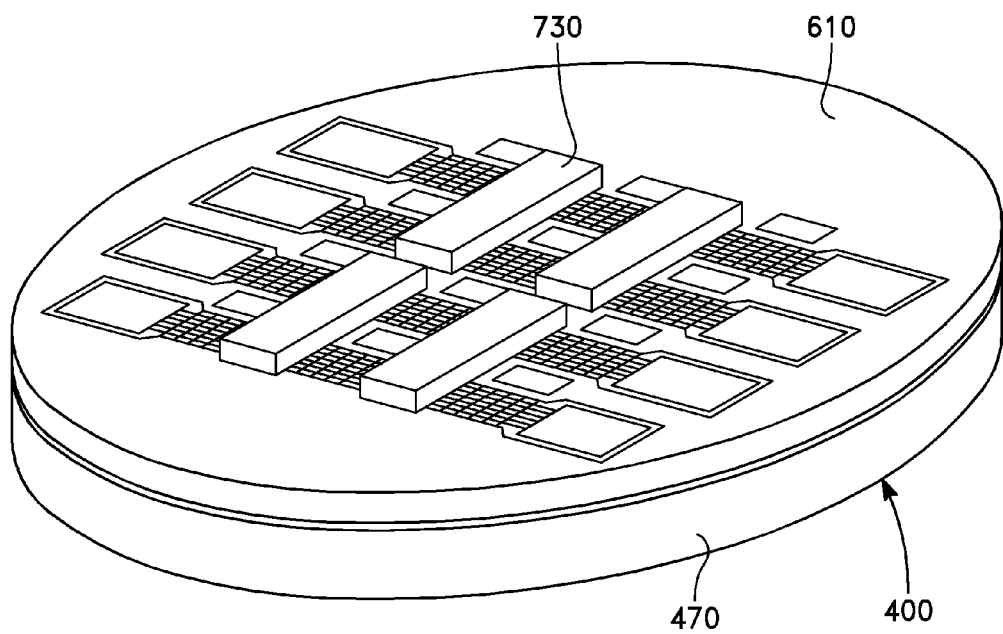

Turning to FIG. 7, while the elastomer net 610 is still on the wafer 470, devices 730 are bonded with a conductive elastomer ink, paste, or other conductive flexible adhesive known in the art (not shown). Examples of conductive elastomer ink are PI-2000 Highly Conductive Silver Ink, by Dow Corning, Midland, Mich., or PI-2310 Conductive Silver Ink, by Dow Corning, Midland, Mich., or ESL 1901-S Polymer Ag Conductor, by ESL ElectroScience, King of Prussia, Pa. Bonding at this stage, while the elastomer net 610 is on the hard mold surface, allows easy transfer to/for pick-and-place machines.

Figure 8:
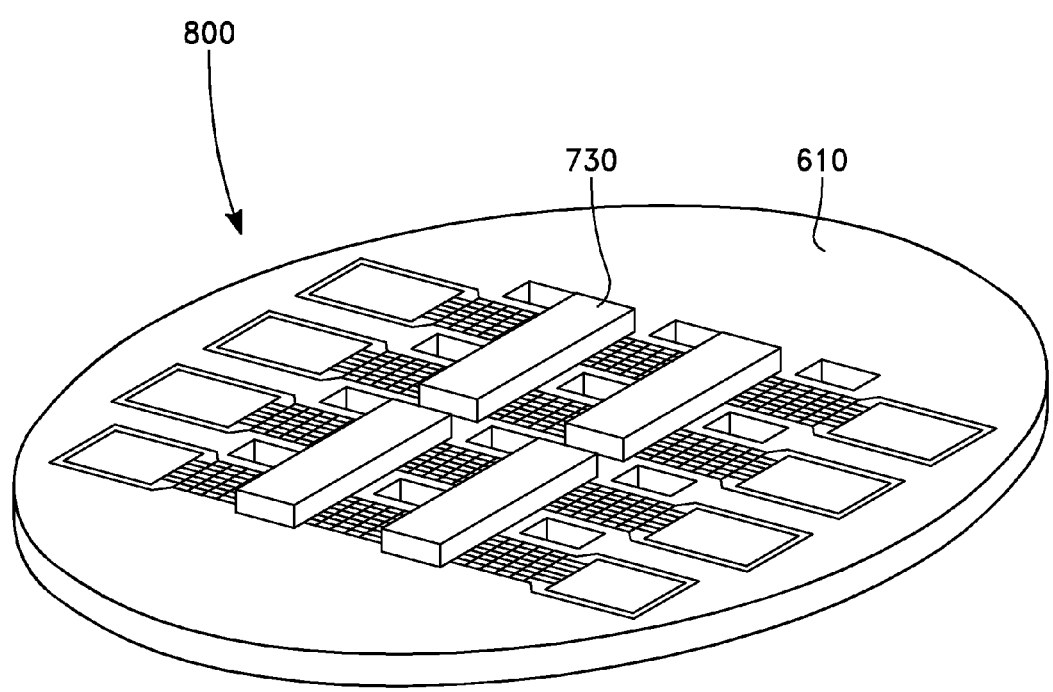

Turning to FIG. 8, the elastomer net 610 mesh with devices 730, is then released from the mold 400 (shown in FIG. 7), with a combination of peeling and dissolving of the mold coat layer 580 (shown in FIG. 5). For example, an OMNICOAT mold coat layer 580, available from Microchem Corp., in Newton, Mass., may be dissolved using isopropanol as the stretchable electronic skin 800 is removed from the mold 400.

For the embodiment of FIG. 2, could be fabricated in a similar fashion, with two iterations of the metal patterning, one for the row and one for the column. An elastomer would be added at the cross-points to prevent shorting between the row column interconnect. A photo-patternable silicone, available from Dow Corning Corp., Midland, Mich., is an example of a material that could be used for the dielectric insulator. In alternate embodiments, the metal could be run or routed along the elastomer net to specific devices on the elastomer net similar to PCB traces.

Referring to FIG. 1, the conductor mesh 120 is a repeating pattern of continuous metal that provides several adjacent connected parallel serpentine paths, i.e. paths repeatedly curving in alternate directions, which form series loops with the adjacent serpentine paths, the loops being connected to adjacent successive loops along a path and to adjacent lateral loop(s). With this pattern, a stretchable planar conductor mesh 120 is formed using conventional deposition techniques that provides a large degree of reversible stretch capability. In one empirical embodiment, the conductor mesh 120 maintained electrical continuity when reversibly stretched by approximately 70% (total area increase) when the stretchable electronic skin 100 was stretched on an inflatable membrane.

In another implementation, a suitable elastic net is imprinted with the conductive mesh, such as by silk screening on the conductive mesh.

Various embodiments of the stretchable electronic skin fabricated with the techniques described herein could be used to cover complex surfaces with e.g. active sensors and associated electronics. The free standing net of the elastomer, metal mesh, and connected electronic devices can be stretched to accommodate the additional surface of a 3-D shape. The stretchable electronic skin of some embodiments fabricated with the above described techniques offer more reversible stretch than previously reported stretchable conductors, without the need to pre-stretch the elastomer during the fabrication process before metal is applied. Various embodiments of the stretchable electronic skin disclosed herein may be formed using planar processing techniques and can be integrated into electronics packing schemes, e.g., pick and place.

Stretchable electronic skin promises unprecedented integrated sensing and local control in applications ranging from microscale tunability of wing surfaces on planes, UAVs, and MUAVS to large scale morphing structures for optimized performance in different use environments, to enhancing human performance with smart clothing and/or engineered exoskeletons. The meso/micro-scale multiple sensors and actuators needed to achieve these systems. require integration of electronics with polymers, specifically elastomers. These skins require more than just flexible wiring; the wiring must be stretchable (even if wireless schemes are used, the antenna coils must be highly conductive and stretchable). The fabrication processes should be scalable to cover large area surfaces and the interconnects must remain conductive under large strains. Shapeable antennas, wings, and the ability to build electronics into the system structure are of keen interest to reduce weight, power consumption, and to offer local sensing and control functionality approaching that of biological skin. This technology is also useful for spherical imaging systems, conformal antenna or RE systems, and retro-modulator systems all of which would benefit from shapeable integrated electronics. Various embodiments provide low interconnect resistance and 3-D shapeability in a scalable design. This is a long-felt need to the realization electronic skins.

Various embodiments could be utilized by unmanned air and ground vehicles, where vehicle size and weight are important, or in fly-by-light power and control of vehicle surfaces where electromagnetic interference (EMI) is of concern. Applications may include automotive, search and rescue, exploration, military defense, or any application where battery weight, power consumption, or electromagnetic interference is a problem, or where safety, system reliability, operating time, observability, operating time, or redundancy impose limitations on a system.

Having described this invention in connection with a number of embodiments, modification will now certainly suggest itself to those skilled in the art. The example embodiments herein are not intended to be limiting, various configurations and combinations of features are possible. As such, the invention is not limited to the disclosed embodiments, except as required by the appended claims.

What is claimed is:

1. A method of fabrication of stretchable electronic skin, the method comprising:
   forming a mold comprising a net pattern on a substrate;
   creating an elastic material net comprising coating the mold with an elastic material precursor;
   forming an elastic conductor mesh on the elastic material net;
   removing the elastic material net with the elastic conductor mesh thereon from the substrate; and
   bonding a device to the elastic conductor mesh.

2. The method of claim 1, wherein forming the elastic conductor mesh comprises depositing a conductor material on the elastic material net.

3. The method of claim 1, wherein forming the elastic conductor mesh comprises depositing a conductor material on the elastic material net using a mask over the elastic material net.

4. The method of claim 1 further comprising creating a planar surface on a top surface of the elastic material precursor.

5. The method of claim 4, wherein forming the mold comprises forming mesas.

6. The method of claim 5, wherein creating the planar surface comprises removing the elastic material precursor from top surfaces of the mesas of the mold.

7. The method of claim 6, wherein creating the planar surface comprises spin coating the mold with elastic material precursor.

8. The method of claim 1, wherein bonding the device to the conductor mesh comprises bonding with a conductive elastomer.

9. The method of claim 8, wherein forming the elastic conductor mesh comprises forming rows and columns of conductor mesh.

10. The method of claim 9, wherein forming the rows and columns comprises forming a multiple layers of elastic conductor mesh.

11. The method of claim 1, wherein forming the mold comprises patterning and etching a silicon substrate.

12. The method of claim 11, wherein forming the mold comprises forming mesas.

13. The method of claim 12, wherein coating the mold comprises spin coating the mold with elastic material precursor, and wherein creating the planar surface comprises removing the elastic material precursor from top surfaces of the mesas of the mold.

14. A method of fabrication of stretchable electronic skin, the method comprising:
   forming a mold comprising a net pattern on a substrate;
   coating the mold with an elastic material precursor;
   planarizing the elastic material precursor;
   solidifying the elastic material precursor to create an elastic material net;
   forming an elastic conductor mesh grid on the elastic material net;
   bonding a device to the conductor mesh grid; and
   removing the elastic net with the elastic conductor and the device thereon from the substrate.

15. A method of fabrication of stretchable electronic skin, the method comprising:
   forming a mold comprising a net pattern on a substrate;
   forming a net comprising elastic material, wherein forming the net comprises coating the mold with an elastic material precursor;
   patterning and forming an elastic conductor on the elastic material of the net;
   bonding a device to the elastic conductor; and
   removing the net with the elastic conductor thereon from the substrate.

* * * * *